(12) United States Patent
Brenner et al.

(10) Patent No.: US 7,449,591 B2
(45) Date of Patent: Nov. 11, 2008

(54) PROCESS OF REMOVING TRANSITION METALS

(75) Inventors: Michael Brenner, Bingen (DE); Kai Donsbach, Hargesheim (DE); Thomas Nicola, Ingelheim (DE); Thomas Wirth, Stadecken-Elsheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 488 days.

(21) Appl. No.: 11/045,406

(22) Filed: Jan. 27, 2005

(65) Prior Publication Data

US 2005/0215423 A1 Sep. 29, 2005

Related U.S. Application Data

(60) Provisional application No. 60/546,130, filed on Feb. 20, 2004.

(30) Foreign Application Priority Data

Jan. 28, 2004 (EP) .................... 04001747

(51) Int. Cl.
C07F 15/00 (2006.01)
B01D 11/00 (2006.01)
(52) U.S. Cl. .................. 556/136; 210/638; 210/639; 210/749; 210/806; 423/658.5
(58) Field of Classification Search ............... 210/634, 210/638, 639, 749, 806; 556/21, 136; 585/833–839, 585/864, 866; 208/252; 423/592.1, 593.1, 423/658.1, 658.5
See application file for complete search history.

(56) References Cited

U.S. PATENT DOCUMENTS

| 4,853,109 | A | * | 8/1989 | Reynolds ............. 208/252 |
| 5,078,858 | A | * | 1/1992 | Hart et al. ............. 208/252 |
| 6,139,814 | A | * | 10/2000 | Shigapov et al. ....... 423/592.1 |
| 6,376,690 | B1 | | 4/2002 | Grubbs et al. |
| 6,608,027 | B1 | | 8/2003 | Tsantrizos et al. |
| 2005/0119453 | A1 | | 6/2005 | Brenner et al. |

FOREIGN PATENT DOCUMENTS

WO    WO 00/59929    10/2000

OTHER PUBLICATIONS

Heather D. Maynard and Robert H. Grubbs, Purification Technique for the Removal of Ruthenium from Olefin Metathesis Reaction Products, Tetrahedron Letters 40 (1999) 4137-4140.
Jong Hyun Cho and B. Moon Kim, An Efficient Method for Removal of Ruthenium Byproducts from Olefin Metathesis Reactions, Organic Letters 2003 vol. 5, No. 4, 531-533.
Yu Mi Ahn, et al, A Convenient Method for the Efficient Removal of Ruthenium Byproducts Generated During Olefin Metathesis Reactions, Organic Letters, 2001, vol. 3, No. 9, 1411-1413.
Leo A. Paquette, et al, A Convenient Method for Removing All Highly-Colored Byproducts Generated During Olefin Metathesis Reactions, Organic Letters, 2000, vol. 2, No. 9, 1259-1261.

* cited by examiner

*Primary Examiner*—Joseph W Drodge
(74) *Attorney, Agent, or Firm*—Michael P. Morris; Mary-Ellen M. Devlin; Philip I. Datlow

(57) ABSTRACT

A process of diminishing the concentration of a transition metal complex from a first solution by adding a solubility-enhancing compound that enhances the solubility of said complex in a second solution and extracting the first solution with the second solution. The solubility-enhancing compound is a compound of formula A

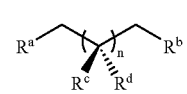

wherein,
$R^a$ is SH, $SO_3H$, OH or COOH;
$R^b$ is SH, OH or COOH;
$R^c$ each independently is H, SH, OH or COOH;
$R^d$ each independently is H or COOH;
n is 1, 2, 3, 4 or 5;
or a salt or an activated form thereof.

19 Claims, No Drawings

PROCESS OF REMOVING TRANSITION METALS

This application claims benefit from U.S. Provisional Application 60/546,130, filed Feb. 20, 2004.

TECHNICAL FIELD

This invention relates to a process of diminishing the concentration of a metal complex from a solution by adding a solubility-enhancing compound that enhances the solubility of said complex in a second solution and extracting the solution containing said complex with the second solution. The solubility-enhancing compound is a compound of formula A

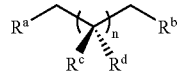

wherein,
$R^a$ is SH, SO$_3$H, OH or COOH;
$R^b$ is SH, OH or COOH;
$R^c$ each independently is H, SH, OH or COOH;
$R^d$ each independently is H or COOH;
n is 1, 2, 3, 4 or 5;

or a salt or an activated form thereof.

BACKGROUND INFORMATION

Despite the ubiquitous use of metal complexes in organic reactions, a simple process for their removal has yet to be discovered. Unfortunately, residual metals often must be removed from the reaction mixture because they can interfere with subsequent transformations and can pose problems for shelf-life and use of the final product.

Current process for removing metal complexes involve running the reactant mixture through numerous columns or other similarly rigorous purification strategies. In addition to being cumbersome, these procedures are time consuming and labour intensive. As uses for metal complexes increases, a simple and facile process for their removal is increasingly needed and desired.

U.S. Pat. No. 6,376,690 discloses a process of removing residual metals from a solution by adding a solubility-enhancing compound, where through the relative solubilities between two solutions are manipulated so as to cause the metal complex in a first solution to transfer into a second solution that is generally immiscible with the first solution. The removal of the second solution thus also removes the metal complex from the reaction mixture.

U.S. Pat. No. 6,376,690 recommend phosphines as useful solubility-enhancing compounds. However, the examples disclosed in this invention, only demonstrate that the use of a special water-soluble phosphine, i.e. trishydroxymethylphosphine (THP) in combination with triethylamine, is able to reduce the Ruthenium content of different simple ether and ester products. With respect to the large scale synthesis of more highly functionalized organic compounds, treatments with THP solutions may cause undesired side reactions. These side reactions may be due to formaldehyde present in THP solutions, which are most easily accessible for large scale operations by means of alkaline deformylation of commercially available aqueous tetrakis(hydroxymethyl)phosphonium salts (TKC).

Moreover, in view of a potential commercial use on large scale, phosphines generally exhibit the disadvantage of being very susceptible towards oxidation. This implies that special measures have to be taken to protect these air sensitive and/or pyrogenic compounds from contact to oxygen and, hence, guarantee their desired efficiency. Hence, these phosphoric compounds are released in situ in separate vessels under inert conditions, increasing the complexity of the large scale processes. In addition, phosphines are toxic and therefore not useful in food or pharmaceutical industry, since any product contamination by these compounds has to be strictly avoided.

Surprisingly it was found, that these pitfalls can be avoided by the use of compounds of formula A

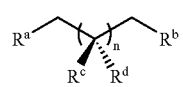

wherein,
$R^a$ is SH, SO$_3$H, OH or COOH;
$R^b$ is SH, OH or COOH;
$R^c$ each independently is H, SH, OH or COOH;
$R^d$ each independently is H or COOH;
n is 1, 2, 3, 4 or 5;

or a salt or an activated form thereof.

BRIEF SUMMARY OF THE INVENTION

The present invention generally relates to the invention that the solubility of metal complexes may be readily manipulated by the addition of a compound of formula A

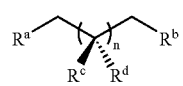

wherein,
$R^a$ is SH, SO$_3$H, OH or COOH;
$R^b$ is SH, OH or COOH;
$R^c$ each independently is H, SH, OH or COOH;
$R^d$ each independently is H or COOH;
n is 1, 2, 3, 4 or 5;

or a salt or an activated form thereof.

In one embodiment of the invention, the relative solubility's between two solutions are manipulated so as to cause the metal complex in a first solution (typically the reaction mixture) to transfer into a second solution that is generally immiscible with the first solution. The removal of the second solution thus also removes the metal complex from the reaction mixture. This embodiment is particularly useful for separating the metal complex from the reaction product.

DETAILED DESCRIPTION OF THE INVENTION

The present invention generally relates to the discovery that the solubility of metal complexes may be readily manipulated by the addition of one or more solubility-enhancing compounds. This manipulation of the solubility's allows for the preparation of suitable samples for precise quantitative analysis and for the facile purification of the desired products from the reaction mixture containing one or more metal complexes.

In the most general sense, the present invention relates to a process of enhancing the solubility of a metal complex (or a combination of metal complexes) in a solution by the addition of one or more solubility-enhancing compounds to the solution.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

As used herein, the term "metal complexes" include the metal compound itself (e.g. Cu, Mg, Ru, Os, etc), its ions, and metal containing or metal associated compounds (either through covalent bounds or through other intermolecular forces such as chelation). Illustrative examples of metal complexes whose solubility's may be manipulated through the practice of the present invention include but are not limited to complexes of: cadmium, chromium, cobalt, copper, gold, iridium, iron, magnesium, manganese, mercury, molybdenum, nickel, osmium, palladium, platinum, rhenium, rhodium, ruthenium, silver, technetium, tungsten, and zinc.

As used herein, "solubility-enhancing compounds" are compounds that interact with a metal or transition complex in a manner that enhances the solubility of the complex in the desired solution. The solubility-enhancing compound can also be activated by a second compound. For example citric acid can be activated by an organic base. Suitable organic bases are dimethylaminopyridine, pyridine, tert. amines, i.e. trimethylamine, triethylamine, diisopropylethylamine or DBU (diazabicycloundecene).

As used herein, "activated forms of solubility-enhancing compounds" are solubility-enhancing compounds that interact with a second compound added to enhance the solubility of the solubility-enhancing compounds in the desired solution. For example, if the desired solution is a polar and/or protic solution, the solubility of a compound, containing acid functions can be enhanced by addition of a base, i.e. citric acid can be activated by an organic base. Suitable organic bases are dimethylaminopyridine, pyridine, tert. amines, i.e. trimethylamine, triethylamine, diisopropylethylamine or DBU (diazabicycloundecene).

As used herein the term "protecting group" includes functional groups used for the protection of a hydroxy function. To protect the hydroxy function the protective group replaces the hydrogen atom of the hydroxy group, to unprotect the hydroxy group cleavage of the group-oxygen bond under reformation of the OH group under mild conditions is possible.

As used herein the term "suitable leaving group" includes functional groups that replace the hydrogen atom of a hydroxy group. Then the group is displaced as stable species taking with it the bonding electrons. Typically the leaving group leaves as an anion taking the oxygen of the former hydroxy group with it. The better the leaving group, the more likely it is to depart.

A leaving group can be the same as a protecting group depending on the reaction to despatch the group. Examples of suitable leaving groups or protecting groups are 2,4,6-trimethylbenzoate, 2,4-dinitrophenyl, 2,4-dinitrophenylsulfenate, 2-chlorobenzoate, 2-trifluoromethylbenzyl, 2-trimethylsilylethyl, 3,4-dimethoxybenzyl, 3,4-dimethoxybenzyl, 3-phenylpropionate, 4-bromobenzoate, 4-nitrobenzoate, 9-anthryl, 9-fluorenylmethyl, □-naphthoate, acetate, allyl, allylsulfonate, benzoylformate, benzyl, benzyloxymethyl, benzylsulfonate, brosylate, chloroacetate, chlorodiphenylacetate, dichloroacetate, diethylisopropylsilyl, dimethylisopropylsilyl, diphenylacetate, diphenylmethyl, ethyl, isobutyl, isobutyrate, menthoxymethyl, methanesulfonate, methoxyacetate, methoxymethyl, methyl, monosuccinoate, nitrobenzyl, nitrophenyl, N-phenylcarbamate, p-acylaminobenzyl, p-chlorophenyl, p-cyanobenzyl, p-halobenzyl, phenoxyacetate, phenylacetate, p-methoxybenzyl, p-methoxyphenyl, p-phenylbenzoate, propargyl, t-butyl, tosylate, tribenzylsilyl, trichloroacetate, triethylsilyl, trifluoroacetate, triisopropylsilyl, trimethylsilyl, triphenylmethyl, triphenylsilyl, tris(trimethylsilyl)silyl, vinyl.

PREFERRED EMBODIMENTS

One embodiment of the invention is a process of diminishing the concentration of a transition metal complex from a first solution containing said complex by the addition of a second solution, comprising the following steps:

a. adding a solubility-enhancing compound that enhances the solubility of said complex in the second solution;

b. combining the first solution with the second solution wherein the second solution is immiscible with the first solution;

c. mixing the first solution and second solution together; and, d. removing the second solution from the first solution;

wherein the solubility-enhancing compound is a compound of formula A

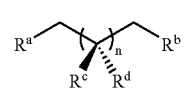

A wherein,
$R^a$ is SH, $SO_3H$, OH or COOH;
$R^b$ is SH, OH or COOH;
$R^c$ each independently is H, SH, OH or COOH;
$R^d$ each independently is H or COOH;
n is 1, 2, 3, 4 or 5;

or a salt or an activated form thereof.

Preferred is a process, wherein a compound of formula A, is used wherein
$R^a$ is $SO_3H$, OH or COOH;
$R^b$ is SH, OH or COOH;
$R^c$ each independently is H, SH, OH or COOH;
$R^d$ each independently is H or COOH;
n is 1, 2, 3, 4 or 5;

Also preferred is a process, wherein a compound of formula A, is used wherein
$R^a$ is SH or OH;
$R^b$ is SH or OH;
$R^c$ each independently is H, SH or OH;
$R^d$ is H;
n is 1, 2, 3 or 4.

Also more preferred is a process, wherein a compound of formula A, is used wherein
$R^a$ is SH;
$R^b$ is SH;
$R^c$ each independently is H or OH;
$R^d$ is H;
n is 1 or 2.

Also preferred is a process, wherein a compound of formula A, is used wherein
$R^a$ is SH or OH;
$R^b$ is SH or OH;
$R^c$ each independently is H, SH or OH;
$R^d$ is H;
n is 1 or 2;

Also preferred is a process, wherein a compound of formula A, is used wherein
$R^a$ is COOH;
$R^b$ is COOH;

$R^c$ each independently is H, OH or COOH;
$R^d$ each independently is H or COOH;
n is 1, 2, 3 or 4;

in the presence of an activating compound of formula $N(R^5)_3$ wherein $R^5$ is $C_{1-6}$-alkyl.

Also preferred is a process, wherein a compound of formula A, is used wherein
$R^a$ is OH or COOH;
$R^b$ is OH or COOH;
$R^c$ each independently is H or OH;
$R^d$ each independently is H or —COOH;
n is 1 or 2;

in the presence of an activating compound of formula $N(R^5)_3$ wherein $R^5$ is $C_{1-6}$-alkyl.

Preferred are the compounds of formula A1,

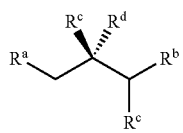

A1 wherein $R^a$, $R^b$, $R^c$, $R^d$ and n have the meaning given for A.

Most preferred is a process, wherein the solubility-enhancing compound is selected from the group consisting of dithioerytrol, 2,3-dimercapto propane-1-sulfonic acid, 2,3-dimercapto succinic acid, citric acid or citric acid in combination with an organic base, selected from the group dimethylaminopyridine, pyridine, triethylamine and diisopropylethylamine.

Preferred is the process wherein the removed transition metal is selected from a group consisting of Cu, Ru, Os, Cd, Cr, Co, Ag, Ir, Fe, Mn, Hg, Mo, Ni, Pd, Pt, Re, Rh, Ag, Te, W or Zn.

More preferred is the process wherein the removed-transition metal is selected from a group consisting of Cu, Ru, Fe, Ni, Pd, Pt, Rh or W, preferably Ru, Pd or Rh, particular preferred is Ru.

Most preferred is a process of diminishing the concentration of a Ru, Rh or Pd complex from a first solution containing said complex by the addition of an aqueous solution, comprising the following steps:
a. adding a solubility-enhancing compound that enhances the solubility of said complex in an aqueous solution;
b. combining the first solution with an aqueous solution wherein the aqueous solution is immiscible with the first solution;
c. mixing the first solution and the aqueous solution together; and,
d. removing the aqueous solution from the first solution;

wherein the solubility-enhancing compound is selected from the group consisting of dithioerytrol, citric acid or citric acid in combination with an organic base, selected from the group dimethylaminopyridine, pyridine, triethylamine and diisopropylethylamine.

In a preferred variation of the above process, an adsorbent is added after removing of the second solution. The process further comprises steps (e) and (f):
e. adding an adsorbent, preferably charcoal powder to the first solution;
f. removing all solid residues from the first solution.

Therefore preferred is a process of diminishing the concentration of a Ru, Rh or Pd complex from a first solution containing said complex by the addition of an aqueous solution, comprising the following steps:
a. adding a solubility-enhancing compound that enhances the solubility of said complex in an aqueous solution; optionally ad an adsorbent;
b. combining the first solution with an aqueous solution wherein the aqueous solution is immiscible with the first solution;
c. mixing the first solution and the aqueous solution together; and,
d. removing the aqueous solution from the first solution;
e. optionally changing the organic solvent from the first solution,
f. adding charcoal powder to the organic solution;
g. removing all solid residues from the organic solution wherein the solubility-enhancing compound is selected from the group consisting of dithioerytrol, citric acid or citric acid in combination with an organic base, selected from the group dimethylaminopyridine, pyridine, triethylamine and diisopropylethylamine.

Another embodiment of the invention is a process for diminishing the concentration of a transition metal complex from a reaction mixture containing said complex, comprising:
a) adding an compound of formula A wherein $R^a$, $R^b$, $R^c$, $R^d$ and n are as defined in claims 1-6, or a salt or a activated form thereof to enhances the solubility of said complex in the second solution;
b) stirring the resulting mixture for 20-720 minutes;
c) extracting the first solution with a second aqueous solution.

Preferred is a process wherein the molar ratio between the transition metal and the solubility enhancing compound is from 1:10 to 1:600, preferably from 1:10 to 1:300, more preferably from 1:25 to 1:100, most preferably about 1:50.

Preferred is a process wherein step b) comprises, stirring the resulting mixture for 60-600 minutes, preferably 180-480 minutes, more preferably 300-420 minutes, most preferably 320-340 minutes.

Preferred is a process wherein step c) comprises:
extracting the first solution once, twice, thrice or more with water or 1-15% $NaHCO_3$ solution in water, preferably water or 2-10% $NaHCO_3$ solution in water, most preferably water or 3-8% $NaHCO_3$ solution in water.

Therefore preferred is a process for diminishing the concentration of a Ru, Rh or Pd complex from a reaction mixture containing said complex, comprising the following steops:
a) adding a compound selected from the group consisting of dithioerytrol, citric acid or citric acid in combination with triethylamine as a solubility-enhancing compound that enhances the solubility of said complex in the second solution;
b) stirring the resulting mixture for 120 minutes;
c) extracting the first solution twice with water.

Preferred is a process, wherein step b) or steps a) and b) are done at 0-100°, preferably 0-60° C., most preferably at room temperature.

Also preferred is a process, wherein the remaining concentration of transition metal after steps a-c is same or less then 1000 ppm, <900 ppm, <800 ppm, preferably <700 ppm, <600 ppm, <500 ppm, in particular <400 ppm, <300 ppm, <200 ppm, <100 ppm, <50 ppm, <10 ppm or <5 ppm.

Preferred is a process wherein step c) is followed by the steps d-g comprising,
d) adding a solid adsorbent;
e) heating the mixture to 20-100° C.
f) stirring the resulting mixture for 10-500 minutes;
g) removing the solid residues.

Preferred is a process wherein the solid adsorbent is charcoal powder.

Preferred is a process wherein step e) comprises, heating the mixture to 30-80° C., preferably 35-70° C., more preferably 40-60° C., most preferably 45-55° C.

Preferred is a process wherein step f) comprises, stirring the resulting mixture for 20-200 minutes, preferably 60-180 minutes, more preferably 100-140 minutes, most preferably 110-130 minutes.

Therefore preferred is a process for diminishing the concentration of a Ru, Rh or Pd complex from a reaction mixture containing said complex, comprising:
a) adding a compound selected from the group consisting of dithioerytrol, citric acid or citric acid in combination with triethylamine as a solubility-enhancing compound that enhances the solubility of said complex in the second solution;
b) stirring the resulting mixture for 120 minutes;
c) extracting the first solution twice with water;
e) adding charcoal powder;
f) heating the mixture to 50° C.
g) stirring the resulting mixture for 120 minutes;
h) filtering the solid residues off.

Also preferred is a process, wherein the remaining concentration of transition metal after steps a-h is same or less then 500 ppm, <400 ppm, preferably <300 ppm, <200 ppm, in particular <100 ppm, <50 ppm, <10 ppm or <5 ppm.

Also preferred is a process, wherein the first solution is the crude product solution of a metathesis reaction containing a compound of general formula 3,

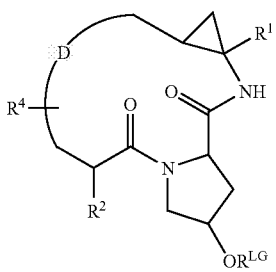

3 wherein $R^1$ is H, $COR^3$, $COOR^3$, CO—$NHR^3$, NH—$COR^3$, NH—$COOR^3$;
$R^2$ is $OR^3$, $NHR^3$, NH—$COR^3$, NH—$CONHR^3$, NH—$COOR^3$;
$R^3$ is H, $C_{1-6}$-alkyl, $C_{3-8}$-cycloalkyl, aryl, het or hetaryl;
$R^4$ is H, $C_{1-6}$-alkyl, $C_{3-8}$-cycloalkyl, OH, SH, $NH_2$, CN, halogen;
$R^{LG}$ is H or a suitable leaving group or protecting group;
D $C_{5-10}$-alkenylene, $C_{5-10}$-alkynylene both optionally containing one, two or three heteroatoms selected from O, S, $NR^3$.

and the source of said transition metal complex is a ruthenium catalyst useful for catalyzing the metathesis reaction. More preferred is a process according wherein product of the metathesis reaction is a compound of general formula 3a,

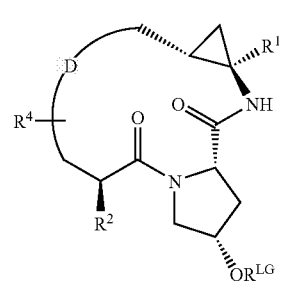

3a wherein $R^1$, $R^2$, $R^4$ and D are defined as above and $R^{LG}$ is a suitable leaving group most preferred is a process, wherein product of the metathesis reaction is a compound of general formula 3b,

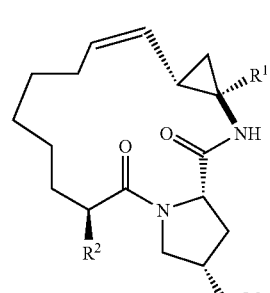

3b wherein $R^{LG}$ is a suitable leaving group and
$R^1$ is H, $COR^3$, $COOR^3$;
$R^2$ is NH—$COR^3$, NH—$CONHR^3$, NH—$COOR^3$;
$R^3$ is H, $C_{1-6}$-alkyl, $C_{3-8}$-cycloalkyl.

Another embodiment of the invention is a process for manufacturing a compound of formula 1

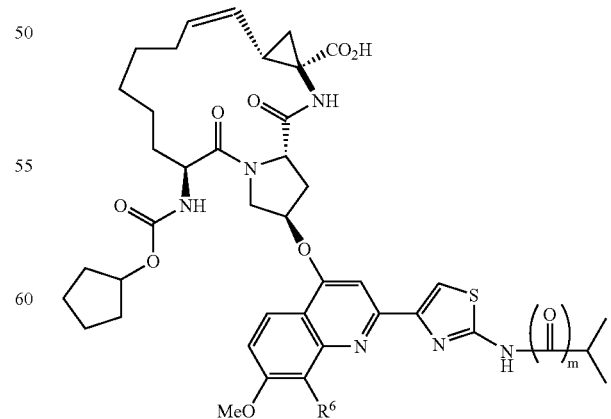

1 wherein $R^6$ is H or $CH_3$ and m is 0 or 1.

comprising,
I) ring closure metathesis reaction of a compound of formula 2 in presence of a useful ruthenium catalyst;

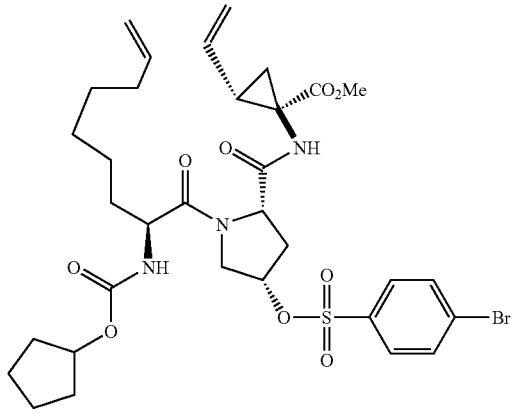

II) diminishing the ruthenium concentration after reaction according to one of the above described procedures;
III) reacting the resulting compound of formula 3c with a compound of formula 4, wherein $R^6$ and m are defined as above;

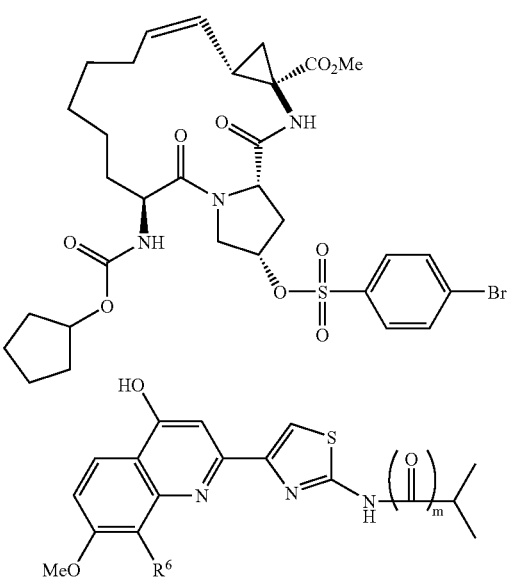

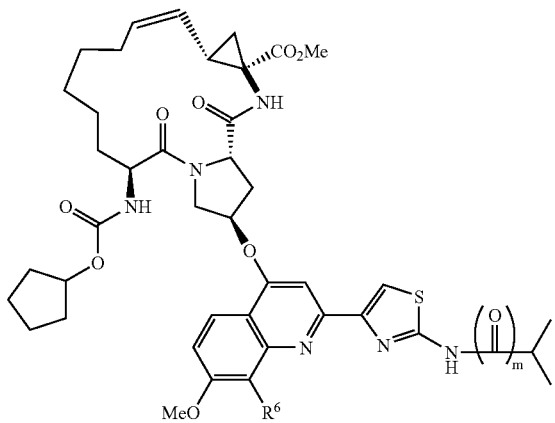

IV) saponification of the resulting compound of formula 5, wherein $R^6$ and m are defined as above;

Preferred is a process for manufacturing a compound 3c comprising ring closure metathesis reaction of a compound 2 in presence of a useful ruthenium catalyst;

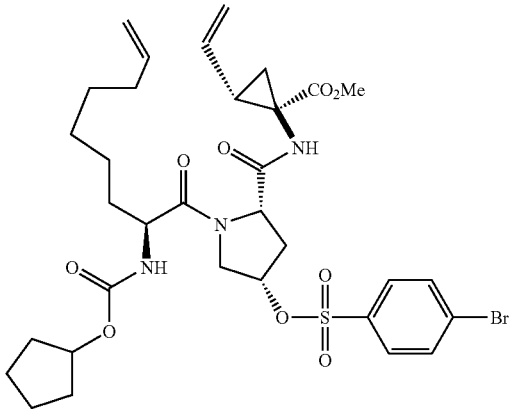

and removing the ruthenium content after reaction according to one of the above described procedures.

This process is particularly effective for the diminishing the concentration of ruthenium complexes, especially of ruthenium complexes containing a metalla-heterocycle, more preferably of ruthenium complexes containing a metalla-heterocycle useful for catalysing metathesis reactions, preferably ring closing metathesis reaction, ring opening metathesis reaction or cross metathesis reaction.

Preferred ruthenium complexes are compounds of formula 6 or 7

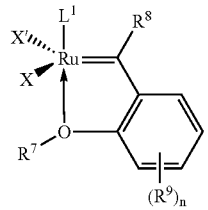

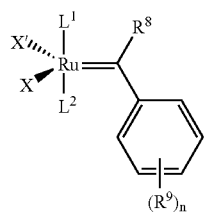

wherein
X and X' are anionic ligands, preferably F, Cl, Br, I, most preferably Cl;
$L^1$ is a neutral ligand, preferably $PCy_3$ or

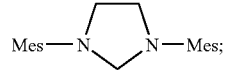

$L^2$ is a neutral ligand, preferably $P(-C_{1-6}\text{-alkyl})_3$, $P(-C_{1-6}\text{-cycloalkyl})_3$ or $PPh_3$, most preferably $PCy_3$
$R^7$ is $C_{1-6}$-alkyl, $C_{1-6}$-haloalkyl, $C_{3-8}$-cycloalkyl or $C_{7-13}$-aralkyl; preferably $C_{1-6}$-alkyl, most preferably iso-propyl;
$R^8$ is H, $C_{1-6}$-alkyl, $C_{2-6}$-alkenyl, $C_{2-6}$-alkynyl or phenyl, most preferably H;
$R^9$ is each independently $C_{1-6}$-alkyl, $C_{1-6}$-alkoxy, phenyl, F, Cl, $NO_2$, CN, $CF_3$, $OCF_3$;
n is 0, 1, 2, 3, 4 or 5;

and Cy has the meaning of cyclohexyl, Mes has the meaning of mesityl.

Most preferred are the ruthenium complexes of formula 6a, 6b and 6c.

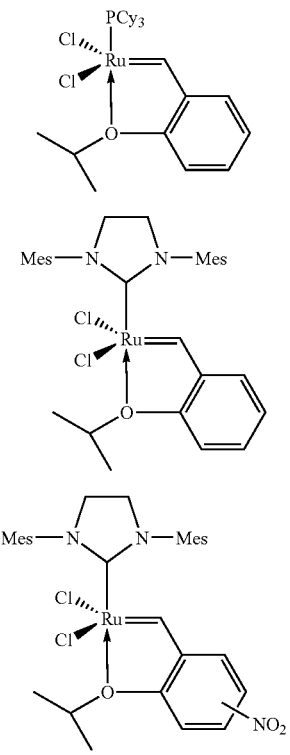

As with prior embodiments, the solubility-enhancing compound may be added to the first solution or the second solution, or the combined solutions. However, it is generally preferred that the solubility-enhancing compound is added to the first solution prior to the combining of the first solution with the second solution.

Although the present invention has been described with examples and references to preferred embodiments, it should be appreciated that the above descriptions were for the purposes of illustration only and not intended in any way to limit the scope of the present invention.

EXPERIMENTAL SECTION

Example 1

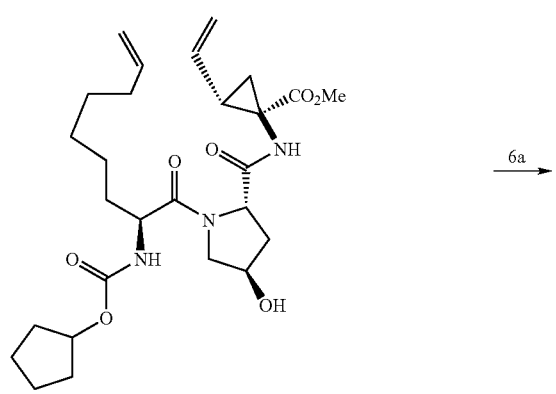

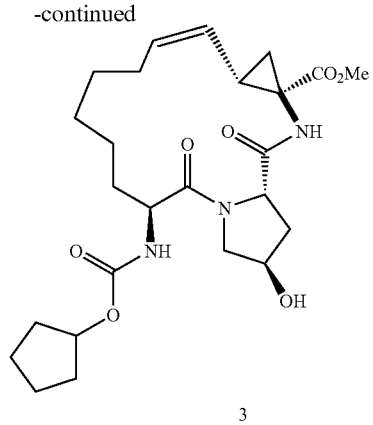

Into a flask, equipped with a mechanical stirrer, a condenser, a nitrogen inlet, a dropping funnel and a heating jacket toluene (21) is added at ambient temperature. The solvent is flushed with nitrogen and heated to 80° C., a 36.3% solution of 2 in toluene (38.8 g), is added to the reactor. After 15 minutes a first portion of solid Hoveyda catalyst 6a (0.136 g) is added, and repeated twice (60 and 120 minutes later); so that the total amount of Hoveyda catalyst at the end is 0.408 g.

After HPLC-analysis indicates >97% conversion of starting material the reaction is stopped by cooling the reactor content to ambient temperature. Three metathesis batches according to Example 1 are combined and further used for metal scavenging experiments.

Example 2

Into a flask, equipped with a mechanical stirrer, a condenser and a heating jacket the clear metathesis solution from Example 1 is added (500 ml, containing ca. 6.6 mmole of 3). The contents are stirred at 25° C., the appropriate metal scavenger (see table 1) is added and the resulting mixture is stirred for the time indicated in table 1. Thereafter the solution is extracted with water, wherein the extraction processes consist of 0.5N $NaHCO_3$ solution in water (1×80 ml) and water (2×100 ml) for Exp. A,B,C, water (1×175 ml) and 5% $NaHCO_3$ solution in water (2×90 ml) for Exp. D. The resulting organic phases are used in the further isolation processes.

Example 3

The toluene solution of metathesis product 3 after watery extraction according to example 2 (ca. 100 mL) is evaporated to dryness (rotary evaporator). The residue is analyzed for its ruthenium content. The results are summarized in table 1 under V3 (B-D).

Example 4

The toluene solution of metathesis product 3 after watery extraction according to example 2 (400 ml) is concentrated to dryness. The residue is dissolved in methanol (80 ml) and water (9 ml). Charcoal powder (1.0 g, Acticarbon LS) is added and the mixture is stirred for 120 minutes at 25° C. The charcoal powder is filtered off and washed with methanol (20 ml). The solvent of the combined organic phases is distilled off and the residue crystallized from a mixture ethyl acetate/methyl cyclohexane (1:25). The yield of isolated metathesis product 3 (white solid) is 2.28-2.51 g (70-77%). The ruthenium content of the metathesis products are listed in table 1 under V4.

TABLE 1

Experimental conditions and results for metal scavenging experiments

| Exp. | scavenger | m [g] (M) [mmole] | Mol % | t [h] | Ru [ppm] V3 | Ru [ppm] V4 |
|---|---|---|---|---|---|---|
| A | none | — | — | — | 5090 | — |
| B | dithioerythrol | 0.14 (0.89) | 5.3 | 2 | 350 | 210 |
| C | dithiothreitol | 0.14 (0.89) | 5.3 | 2 | 980 | 270 |
| D | citric acid mono hydrate | 1.40 (6.64) | 40 | 24 | 620 | 310 |
|   | triethylamine | 2.21 (19.2) | | | | |

What is claimed is:

1. A process for diminishing the concentration of a transition metal complex in a first solution containing said complex by the addition of a second solution, comprising the steps:
   (a) adding to the first solution a solubility-enhancing compound that enhances the solubility of said complex in the second solution;
   (b) combining the first solution with the second solution wherein the second solution is immiscible with the first solution;
   (c) mixing the first solution and second solution together; and,
   (d) removing the second solution from the first solution;
wherein the solubility-enhancing compound is a compound of formula A

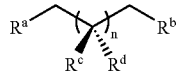

wherein,
   $R^a$ is SH, or OH;
   $R^b$ is SH, or OH;
   $R^c$ each independently is H, SH, or OH;
   $R^d$ each is H;
   n is 1, 2, 3, or 4;
   or a salt or an activated form thereof.

2. A process according to claim 1, wherein in the compound of formula A:
   $R^a$ is SH;
   $R^b$ is SH;
   $R^c$ each independently is H or OH;
   $R^d$ is H;
   n is 1 or 2.

3. A process according to claim 1, wherein in the compound of formula A:
   $R^a$ is OH;
   $R^b$ is OH;
   $R^c$ each independently is H or OH;
   $R^d$ each is H;
   n is 1 or 2;
   and the process is performed in the presence of an activating compound of formula $N(R^5)_3$ wherein $R^5$ is $C_{1-6}$-alkyl.

4. A process according to claim 1, wherein the metal of said metal complex is selected from the group consisting of Cu, Ru, Fe, Ni, Pd, Pt, Rh and W.

5. A process according to claim 1, wherein the molar ratio of transition metal and solubility-enhancing compound is between 1:10 and 1:600.

6. A process according to claim 1, wherein step c) comprises, stuffing the resulting mixture for 300-420 minutes.

7. A process according to claim 1, wherein step d) comprises:
   extracting the first solution with 5% $NaHCO_3$ in water; and
   extracting the first solution at least twice with water.

8. A process according to claim 1, wherein the remaining concentration of transition metal after steps a)-d) is less then 1000 ppm.

9. A process for diminishing the concentration of a transition metal complex in a first solution containing said complex by the addition of a second solution, comprising:
   (a) adding to the first solution a solubility-enhancing compound that enhances the solubility of said complex in the second solution;
   (b) combining the first solution with the second solution wherein the second solution is immiscible with the first solution;
   (c) mixing the first solution and second solution together;
   (d) removing the second solution from the first solution;
   (e) adding charcoal powder to the resulting first solution; and
   (f) removing all solid residues from the first solution;
wherein the solubility-enhancing compound is a compound of formula A

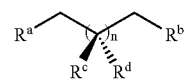

wherein,
   $R^a$ is SH, $SO_3H$, OH or COOH;
   $R^b$ is SH, OH or COOH;
   $R^c$ each independently is H, SH, OH or COOH;
   $R^d$ each independently is H or COOH;
   n is 1, 2, 3, 4 or 5;
   or a salt or an activated form thereof.

10. A process for diminishing the concentration of a transition metal complex in a first solution containing said complex by the addition of a second solution, comprising,
   (a) adding to the first solution a solubility-enhancing compound that enhances the solubility of said complex in the second solution;
   (b) combining the first solution with the second solution wherein the second solution is immiscible with the first solution;
   (c) mixing the first solution and second solution together;
   (d) removing the second solution from the first solution;
   e) adding a solid adsorbent;
   f) heating the mixture to 20-100° C.;
   g) stirring the resulting mixture for 10-500 minutes; and
   h) removing the solid residues;
wherein the solubility-enhancing compound is a compound of formula A

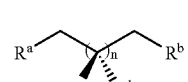

wherein,
   $R^a$ is SH, $SO_3H$, OH or COOH;
   $R^b$ is SH, OH or COOH;
   $R^c$ each independently is H, SH, OH or COOH;
   $R^d$ each independently is H or COOH;
   n is 1, 2, 3, 4 or 5;
   or a salt or an activated form thereof.

11. A process according to claim 10, wherein the solid adsorbent is charcoal powder.

12. A process according to claim 10, wherein step f) comprises heating the mixture to 45-55° C.

13. A process according to claim 10, wherein step g) comprises stirring the resulting mixture for 100-140 minutes.

14. A process according to claim 10, wherein the remaining concentration of transition metal after steps a-h is less then 500 ppm.

15. A process for diminishing the concentration of a transition metal complex in a first solution containing said complex and a product of a metathesis reaction, comprising the following steps:
   a) adding to the first solution a solubility-enhancing compound of formula A, or a salt or activated form thereof, to enhance the solubility of said complex in an aqueous solution, immiscible with the first solution;
   b) stirring the resulting mixture for 60-600 minutes; and
   c) extracting the reaction mixture with the aqueous solution;
wherein the solubility-enhancing compound of formula A is

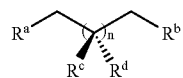

A wherein,
   $R^a$ is SH, or OH;
   $R^b$ is SH, or OH;
   $R^c$ each independently is H, SH, or OH;
   $R^d$ each is H;
   n is 1, 2, 3, 4 or 5.

16. A process according to claim 15, wherein the first solution is a crude product solution of a metathesis reaction containing a compound of formula 3,

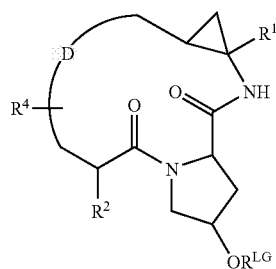

3 wherein
   $R^1$ is H, $COR^3$, $COOR^3$, CO—$NHR^3$, NH—$COR^3$, NH—$COOR^3$;
   $R^2$ is $OR^3$, $NHR^3$, NH—$COR^3$, NH—$CONHR^3$, NH—$COOR^3$;
   $R^3$ is H, $C_{1-6}$-alkyl, $C_{3-8}$-cycloalkyl, aryl, het or hetaryl;
   $R^4$ is H, $C_{1-6}$-alkyl, $C_{3-8}$-cycloalkyl, OH, SH, $NH_2$, CN, halogen;
   $R^{LG}$ is H or a suitable leaving group or protecting group; and
   D $C_{5-10}$-alkenylene or $C_{5-10}$-alkynylene both optionally containing one, two or three heteroatoms selected from O, S, and $NR^3$, and the source of said transition metal complex is a ruthenium catalyst useful for catalyzing the metathesis reaction.

17. A process according to claim 16, wherein the compound of formula 3 is a compound of formula 3a,

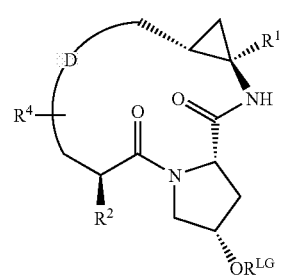

3a wherein $R^1$, $R^2$, $R^4$, and D are defined as in claim 16; and $R^{LG}$ is a suitable leaving group.

18. A process according to claim 16, wherein the compound of formula 3 is a compound of formula 3b;

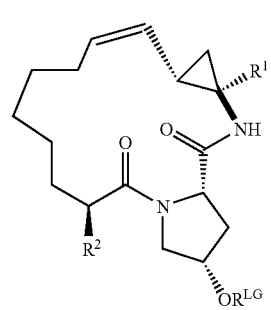

3b wherein
   $R^1$ is H, $COR^3$, $COOR^3$;
   $R^2$ is NH—$COR^3$, NH—$CONHR^3$, NH—$COOR^3$;
   $R^3$ is H, $C_{1-6}$-alkyl, $C_{3-8}$-cycloalkyl; and
   $R^{LG}$ is a suitable leaving group.

19. A process for manufacturing a compound of formula 1

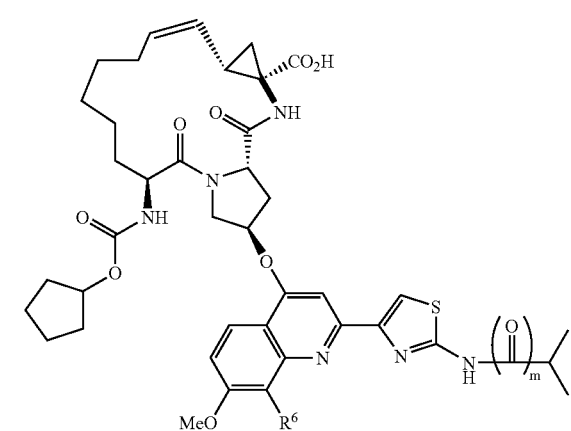

1 wherein $R^6$ is H or $CH_3$ and m is 0 or 1, said process comprising:

I) ring-closing a compound of formula 2 in presence of a ruthenium catalyst:

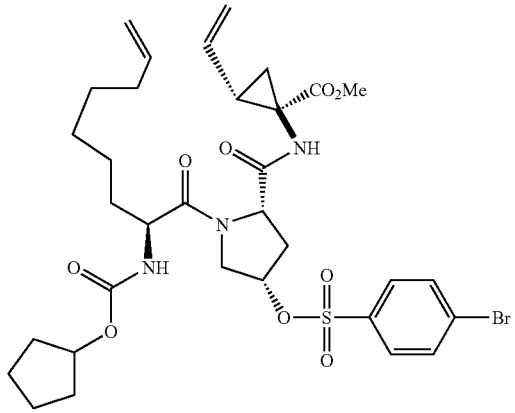

2

II) diminishing the ruthenium concentration in the resulting reaction mixture by the addition of a second solution according to a method comprising:
(a) forming a first solution by adding to the reaction mixture a solubility-enhancing compound that enhances the solubility of said complex in the second solution;
(b) combining the first solution with the second solution wherein the second solution is immiscible with the first solution;
(c) mixing the first solution and second solution together; and,
(d) removing the second solution from the first solution;
wherein the solubility-enhancing compound is a compound of formula A

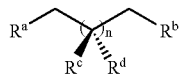

A wherein,
$R^a$ is SH, or OH;
$R^b$ is SH, or OH;
$R^c$ each independently is H, SH, or OH;
$R^d$ each is H;
n is 1, 2, 3, 4 or 5;
or a salt or an activated form thereof;
III) reacting the resulting compound 3c with a compound of formula 4, wherein $R^6$ and m are defined as above:

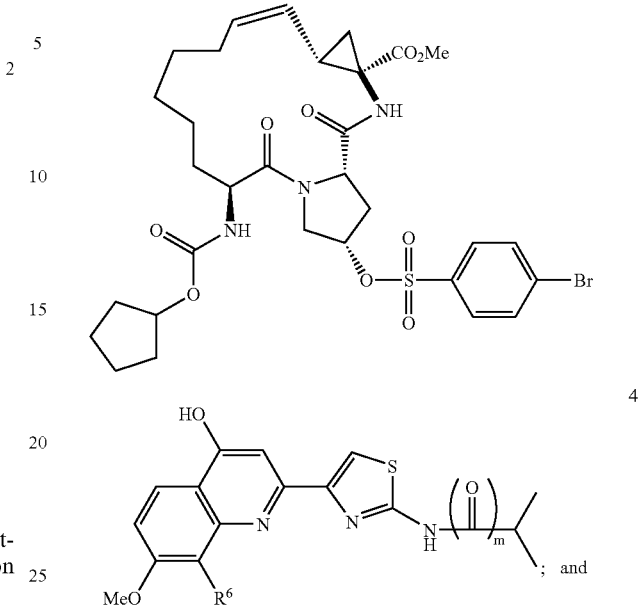

IV) saponifying the resulting compound of formula 5, wherein $R^6$ and m are defined as above; to obtain a compound of formula 1 as defined above:

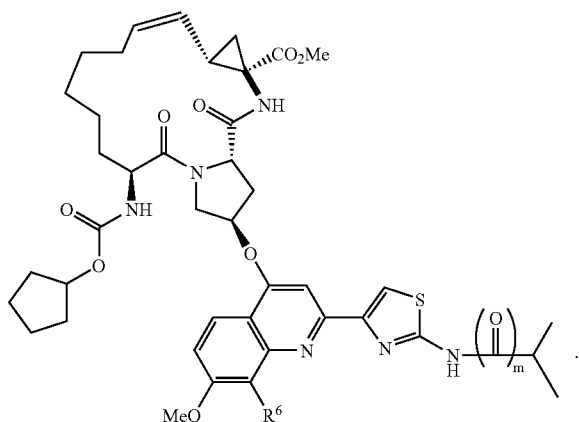

* * * * *